United States Patent
Kuan et al.

(10) Patent No.: US 9,612,203 B2
(45) Date of Patent: *Apr. 4, 2017

(54) DETECTION DEVICE AND MANUFACTURING METHOD FOR THE SAME

(71) Applicant: National Tsing Hua University, Hsinchu (TW)

(72) Inventors: Chen-Meng Kuan, Hsinchu (TW); Roger L. York, Hsinchu (TW); Robert S. Langer, Hsinchu (TW); Chao-Min Cheng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 37 days.

This patent is subject to a terminal disclaimer.

(21) Appl. No.: 14/618,713

(22) Filed: Feb. 10, 2015

(65) Prior Publication Data

US 2015/0153286 A1    Jun. 4, 2015

Related U.S. Application Data

(63) Continuation-in-part of application No. 13/945,237, filed on Jul. 18, 2013, now Pat. No. 9,063,128.

(30) Foreign Application Priority Data

Jun. 25, 2013    (TW) .............................. 102122514 A

(51) Int. Cl.
G01N 21/78      (2006.01)
G01N 33/52      (2006.01)
C12Q 1/54       (2006.01)

(52) U.S. Cl.
CPC ............... *G01N 21/78* (2013.01); *C12Q 1/54* (2013.01); *G01N 33/52* (2013.01); *G01N 33/528* (2013.01)

(58) Field of Classification Search
None
See application file for complete search history.

(56) References Cited

U.S. PATENT DOCUMENTS 3,552,928 A      1/1971 Fetter
4,960,548 A *  10/1990 Ikeda ....................... B27N 3/22
                                                   209/139.1
8,044,257 B2 * 10/2011 Song ...................... G01N 33/558
                                                   604/361
2005/0112023 A1 * 5/2005 Liang .................. G01N 33/558
                                                   422/400
2010/0159599 A1   6/2010 Sont et al.
2013/0034869 A1   2/2013 Whitesides et al.

FOREIGN PATENT DOCUMENTS

| CN | 2448221 Y | * | 9/2001 | ........... A47G 21/103 |
| CN | 101957354 A | | 1/2011 | |
| CN | 104111327 A | | 10/2014 | |
| TW | 201017165 A | | 5/2010 | |
| TW | 201226904 A | | 7/2012 | |
| TW | 201317361 A | | 5/2013 | |

OTHER PUBLICATIONS

Pettersen, R.C. 1984. The chemical composition of wood. In: The chemistry of solid wood. Advances in chemistry series 207. Chapter 2. Ed.: Rowell, Roger M. . Published by the American Chemical Society, Wash. DC. pp. 57-126. specif. p. 57.*
Eng. translation—Abuduazizi, A. Chinese Patent Application Publication No. CN2448221Y, Sep. 19, 2001. Sanitary hollow plastic chopticks. pp. 1-3. specif. pp. 1, 2, 3.*
Via, B.K. et al. 2009. Mechanical reponse of longleaf pine to variation in microfibril angle, chemistry associated wavelengths, density, and radial position. Composites: Part A 40: 60-66. specif. pp. 61, 63, 64.*
Pelton, R. 2009. Bioactive paper provides low-cost platform for diagnostics. Trends in Analytical Chemistry 28(8): 925-942. specif. pp. 926, 929.*
Sun, Y. et al. 2002. Hydrolysis of lignocellulosic materials for ethanol production: a review. Biosource Technology 83: 1-11, specif. p. 2.
Dr. Chao-Min Cheng, "Cellulose-based Diagnostic Devices for Public Health and Food Safety", Institute of NanoEngineering and MicroSystems & Department of Power Mechanical Engineering, Feb. 17, 2014, pp. 1-67.

* cited by examiner

*Primary Examiner* — Renee Claytor
*Assistant Examiner* — Sharon M Papciak
(74) *Attorney, Agent, or Firm* — Muncy, Geissler, Olds & Lowe, P.C.

(57) ABSTRACT

A detection device includes a xylem fiber substrate configured with a sampling portion and a reaction portion. The reaction portion includes at least one enzyme reagent. The sampling portion absorbs a test sample. The test sample moves on the xylem fiber substrate to the reaction portion and reacts with the enzyme reagent. A manufacturing method for the detection device is also disclosed. The detection device is advantageous for easy operation, safety and rapid analysis.

12 Claims, 9 Drawing Sheets

DETECTION DEVICE AND MANUFACTURING METHOD FOR THE SAME

CROSS REFERENCE TO RELATED APPLICATIONS

This application is a Continuation-In-Part (CIP) of an earlier filed, pending, application, having application Ser. No. 13/945,237 and filed on Jul. 18, 2013, the content of which, including drawings, is expressly incorporated by reference herein.

BACKGROUND OF THE INVENTION

Field of Invention

The present invention relates to a detection device and a manufacturing method for the same. More particularly, the present invention relates to a detection device used for detecting food safety and a manufacturing method for the same.

Related Art

As the rising of health consciousness, the concept of self-detection in house is more and more popular. The self-detection allows the users to easily and simply detect the simple physiological status or the food safety anytime and anywhere. The detection of physiological status can help the general users to check the health statuses of themselves and, in particular, assist the patients to enhance the therapeutic effects and to control the diseases progressions. The food safety detections have become more and more important. This is because the food products may contain some remained bad substances, which exist in the raw materials or are generated during the manufacturing processes. Therefore, it is desired to effectively detect the food additives before tasting food products.

Regarding to the self-detection technology, the detection device usually utilizes the color change of detection reagent, which can be determined by naked eyes or simple equipment, to indicate the detection result within a short time. Therefore, the self-detection technology has the advantages of easy operation, fast detection, and low cost.

Although this simple detection method brings the users an extremely large convenience and safety, the users have to carry the testing strips all the time, which may bother the users indeed. In addition, the existing testing strips are almost made by many processes, and the added substances in the testing strips will cause the risk of the safety of the testing strips.

Besides, some daily necessities, such as the stirring rods, toothpicks or chopsticks, are mostly made by natural raw materials. However, these artificial products cannot provide additional functions.

Therefore, it is an important subject to provide a detection device, which has the simple operation property as the existing testing strips, is capable of being applied to daily necessities and adopts special and natural material for improving the sampling and detecting speeds and the application safety, and a manufacturing method thereof.

SUMMARY OF THE INVENTION

In view of the foregoing subject, an objective of the present invention is to provide a detection device, which has the simple operation property as the existing testing strips, is capable of being applied to daily necessities and adopts special and natural material for improving the sampling and detecting speeds and the application safety, and a manufacturing method thereof.

To achieve the above objective, the present invention discloses a detection device including a xylem fiber substrate configured with a sampling portion and a reaction portion. The reaction portion has at least an enzyme reagent. The sampling portion absorbs a test sample. The test sample moves on the xylem fiber substrate to the reaction portion and reacts with the enzyme reagent.

In one embodiment, the xylem fiber substrate comprises cellulose, lignin or hemicellulose.

In one embodiment, the enzyme reagent comprises a glucose reagent, a lactic acid reagent, a hydrogen peroxide reagent, a glycogen reagent or a nitrate reagent.

In one embodiment, the detection device is a stirring rod, a toothpick or a chopstick.

In one embodiment, the reaction portion has an accommodating space and a bulk body, the accommodating space is formed on a surface of the xylem fiber substrate, at least a part of the bulk body is disposed in the accommodating space, and the enzyme reagent is disposed on the bulk body.

In one embodiment, the accommodating space is disposed between two separate parts on the surface of the xylem fiber substrate, and the two separate parts are at least partially connected to each other.

In one embodiment, the proportion of α-cellulose in the bulk body is greater than that in the reaction portion.

In one embodiment, the densification property of the bulk body is greater than that of the reaction portion.

To achieve the above objective, the present invention also discloses a manufacturing method for a detection device. The manufacturing method includes the steps of: providing a xylem fiber substrate; forming a sampling portion and a reaction portion on the xylem fiber substrate; and disposing at least an enzyme reagent in the reaction portion so as to form the detection device.

In one embodiment, the step of providing the xylem fiber substrate includes to provide a raw material containing xylem fiber and to physically process the raw material to extract the xylem fiber substrate.

In one embodiment, the xylem fiber substrate comprises cellulose, lignin or hemicellulose.

In one embodiment, before the step of providing the xylem fiber substrate, the manufacturing method further includes a step of: shaping the xylem fiber substrate to a shape of stirring rod, a toothpick or a chopstick.

In one embodiment, the manufacturing method further includes the steps of: forming an accommodating space and a bulk body in the reaction portion, wherein the accommodating space is formed on a surface of the xylem fiber substrate, and at least a part of the bulk body is disposed in the accommodating space; and disposing the enzyme reagent on the bulk body.

In one embodiment, the accommodating space is formed between two separate parts on the surface of the xylem fiber substrate, and the two separate parts are at least partially connected to each other.

In one embodiment, the proportion of α-cellulose in the bulk body is greater than that in the reaction portion.

In one embodiment, the densification property of the bulk body is greater than that of the reaction portion.

As mentioned above, the detection device of the present invention has a reaction portion containing the enzyme reagent for effectively detecting a specific test target such as the concerned nitrate in food safety or the glucose detection in the biomedical detection field. The detection device includes a main structure composed of xylem fiber substrate, which has excellent absorptive property for water molecules, so that the capillary phenomenon of the liquid test sample in the detection device can be enhanced.

In addition, the conventional testing strips, which are made by multiple processes, may contain some residual prohibited or harmful chemical reagents used in the processes, so the food products cannot be served after being detected by the conventional testing strips. In contrary, the detection device of the invention is made of the natural xylem fiber substrate, which has much less influence to the test sample, so the test sample can be still served after the detection. Besides, the present invention also has the advantages of lower cost and easy production. Preferably, the xylem fiber substrate has a strengthened mechanical structure and better pH durability than the conventional testing strips (made by papers).

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
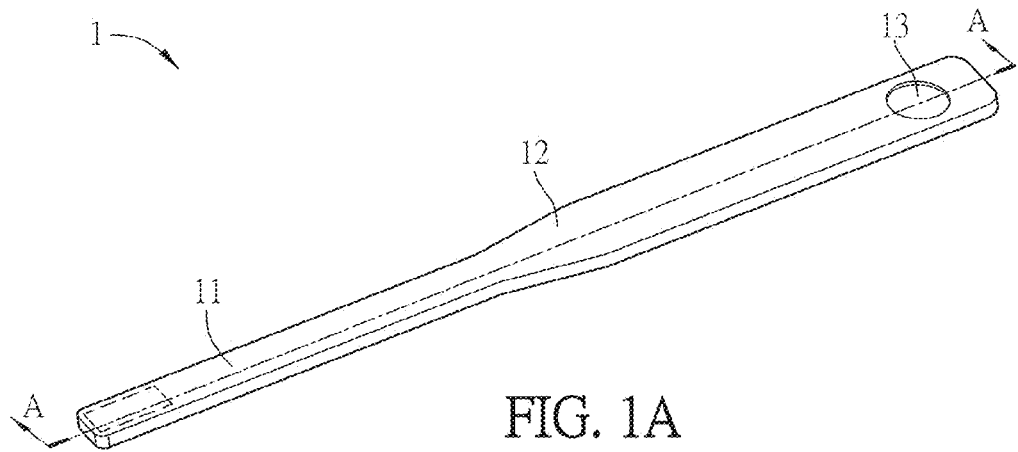
FIG. 1A is a schematic diagram of a detection device according to a preferred embodiment of the invention.
Figure 1B:
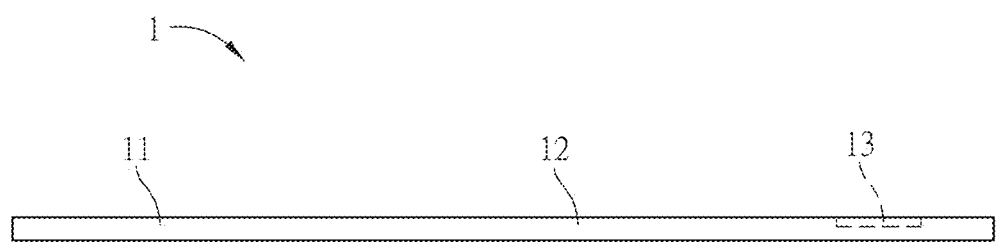
FIG. 1B is a sectional view along the line A-A of FIG. 1A.

FIG. 1A is a schematic diagram of a detection device according to a preferred embodiment of the invention, and FIG. 1B is a sectional view along the line A-A of FIG. 1A. Referring to FIGS. 1A and 1B, the detection device 1 of the embodiment is used to sample and detect a test sample, which is for example but not limited to a biological fluid (e.g. blood sample) or food product (e.g. the soup of hot pot). Accordingly, the detection device 1 can be used as a biomedical detection device or a food safety detection device.

The detection device 1 can be functioned as a stirring rod, a chopstick, a toothpick or the likes so as to be properly applied to the daily necessities. That is, the detection device 1 can be functioned as a stirring rod, a chopstick or a toothpick, and also have the additional detection function. In other words, the above examples are essential products for many users, which means that the users do not have to carry any additional necessity along with themselves for the detection purpose. In this embodiment, the detection device 1 is a stirring rod as an example.

Figure 2:
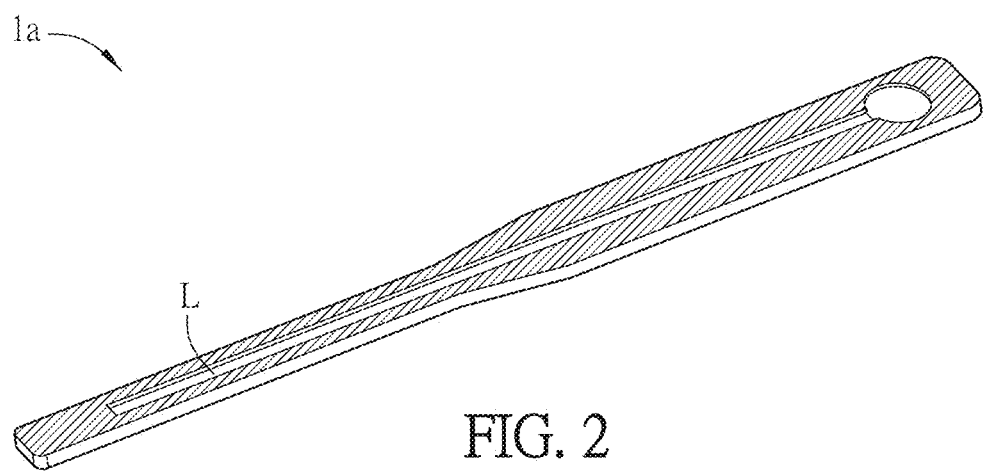
FIG. 2 is a schematic diagram of a detection device according to another preferred embodiment of the invention.

Referring to FIGS. 1A and 1B, the detection device 1 of the embodiment has a xylem fiber substrate. In other words, the detection device 1 is a structure at least partially made by the xylem fiber substrate. In the practice manufacturing procedure, the detection device 1 is preferably made by the xylem fiber substrate entirely. Of course, the concept of this invention also includes the case that the detection device has only a part to be made by the xylem fiber substrate for transmitting the test sample (a "flowing channel"). As shown in FIG. 2, the detection device 1a has a channel structure L extending along the axial direction thereof. The channel structure L is entirely made by the xylem fiber substrate, and the residual part of the detection device 1a other than the channel structure L may include any suitable material other than the xylem fiber substrate. The material of the residual part has a hydrophilic property poorer than the xylem fiber substrate, and this invention is not limited.

Regarding to the major functional compositions, the xylem fiber substrate of the detection device 1 is configured with a sampling portion 11, a transmission portion 12 and a reaction portion 13. The sampling portion 11, the transmission portion 12 and the reaction portion 13 are adjacently disposed in sequence. In practice, the shape and size of each portion are not limited, and they can be designed based on the test sample or the detection target. The actual shape of each portion can be, for example but not limited to, cylinder, rectangular or plate, and this invention is not limited. In brief, the sampling portion 11 can absorb the test sample, and then the test sample moves to the reaction portion 13 on the xylem fiber substrate for performing the following reaction. The means for "absorbing" the test sample includes the approach of: directly dipping the sampling portion 11 into the test sample so that the sampling portion 11 can directly absorb the test sample; or using an auxiliary tool (e.g. a pipette or a needle) to retrieve the test sample and then dropping it onto the sampling portion 11, so that the sampling portion 11 can absorb the test sample.

Herein, the term "xylem fiber substrate" means the woody fibrous tissue of a plant. In this invention, the xylem fiber substrate includes cellulose, hemicellulose, pectin or lignin, which has better absorption property for water molecules. Accordingly, the test sample can be transmitted from the sampling portion 11 to the reaction portion 13 through the transmission portion 12 (via the pores in the xylem fiber substrate).

The raw material of the detection device 1 can be a wood or bamboo piece, and preferably selected from any woody plant with high-degree woody tissues such as shrubs or arbors. In practice, the stirring rod, chopstick or toothpick made by the woody tissue can be further processed to obtain the detection device 1. Since the conventional testing strips may contain some residual prohibited or harmful chemical reagents used in the manufacturing processes, so the food products cannot be served after being detected by the conventional testing strips. In contrary, the detection device 1 of the embodiment is made of a xylem fiber substrate, which is a natural material and has higher safety. During the detection, the detection device 1 can be directly applied to or inserted into a sample and the tested sample can be still served after the detection without any additional treatment (e.g. the treatment for removing remained chemical reagent or harmful substances). Besides, the xylem fiber substrate is a natural material, so it has the advantages of lower cost and easy processing.

In addition, the xylem fiber substrate has a strengthened mechanical structure and better pH durability than the conventional testing strips (made by papers).

With reference to FIGS. 1A and 1B, the test sample is transmitted to the reaction portion 13 through the transmission portion 12. In order to remove the impurity in the test sample for enhancing the detection accuracy, the sampling portion 11 can be configured with a filter layer (as the dotted line area of FIG. 1A). The shape, size and location of the filter layer can be designed according to the actual need and is not limited in this embodiment. For example, when the amount of the test samples is quite large, a large sized filter layer can be selected for improving the filtering effect.

Figure 3:
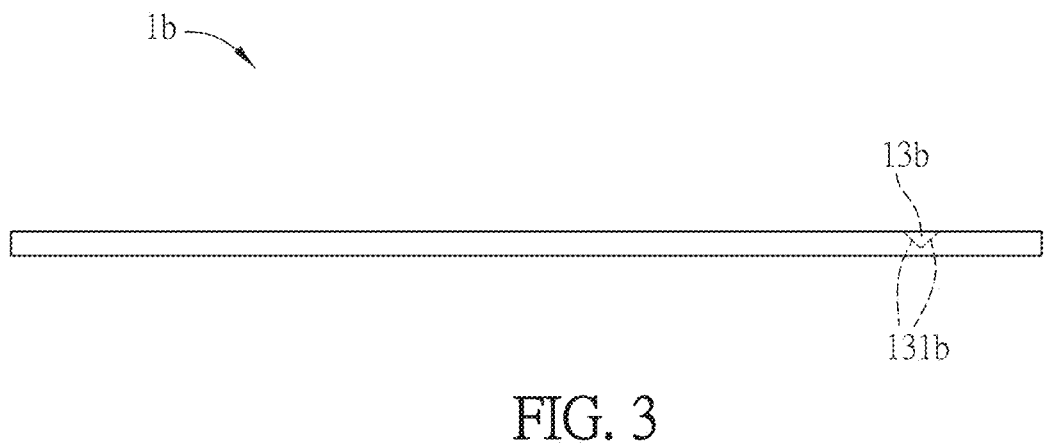
FIG. 3 is a sectional view of a detection device according to another preferred embodiment of the invention.

In this embodiment, the reaction portion 13 is a recess. The shape and size of the recess can be designed according to the actual need and is not limited in this embodiment. The recess shown in FIGS. 1A and 1B is for an illustration only and is not to limit the scope of the invention. In practice, the shape of the reaction portion 13 can be, for example but not limited to, rectangular, square, cylinder, hemisphere, V-shape, or any other suitable shapes. As shown in FIG. 3, the reaction portion 13b of the detection device 1b is V-shaped. This structure is helpful to observe the color result on the side wall 131b, thereby improving the accuracy of the detection. To be noted, the location of the reaction portion is flexible depending on the detection requirement, and this invention is not limited.

In order to achieve the detection purpose, a plurality of enzyme reagents is configured in the reaction portion 13. Since the detection device 1 is applied to food safety detection and biomedical detection, the detection targets of the detection device 1 may include, for example, the food raw materials or the residual substances from the manufacturing processes, such as the food additive reagent, or the important detection items in biomedical detection (e.g. blood sugar).

Herein, the enzyme reagents are firmly or unfirmly disposed in the reaction portion 13. The means for firmly disposing the enzyme reagent in the reaction portion 13 includes to connect a specific functional group of the enzyme reagent to the reaction portion 13 by, for example but not limited to, covalent bonds. The means for unfirmly disposing the enzyme reagent in the reaction portion 13 includes to dispose the enzyme reagent in the reaction portion 13 by coating or the likes.

As shown in FIG. 1B, the enzyme reagent is disposed on the bottom of the reaction portion 13, but this invention is not limited thereto. In other embodiments, the enzyme reagent can be disposed at the side surface of the reaction portion 13 only or be disposed at the side surface and bottom of the reaction portion 13 both.

After configuring the detection device 1, it can be used to detect food products later. In practice, the user can bring the detection device 1 (the sampling portion 11) to contact the test sample or drop the test sample on the sampling portion 11, then the test sample will be transmitted from the sampling portion 11 to the reaction portion 13 through the transmission portion 12 by capillary action. If the test sample contains nitrite, it will react with the chemical reagent in the reaction portion 13 to generate purple red azo compound. Accordingly, the detection device 1 can detect whether the test sample contains nitrite or not, thereby improving the personal safety. Of course, if it is desired to determine whether the contained amount of nitrite in the test sample is over the safety limitation, the detection device 1 can also provide a quantification function by colorimetric method. Preferably, the detection device 1 of the invention is designed in the form of daily necessities so as to increase the convenience.

Figure 4A:
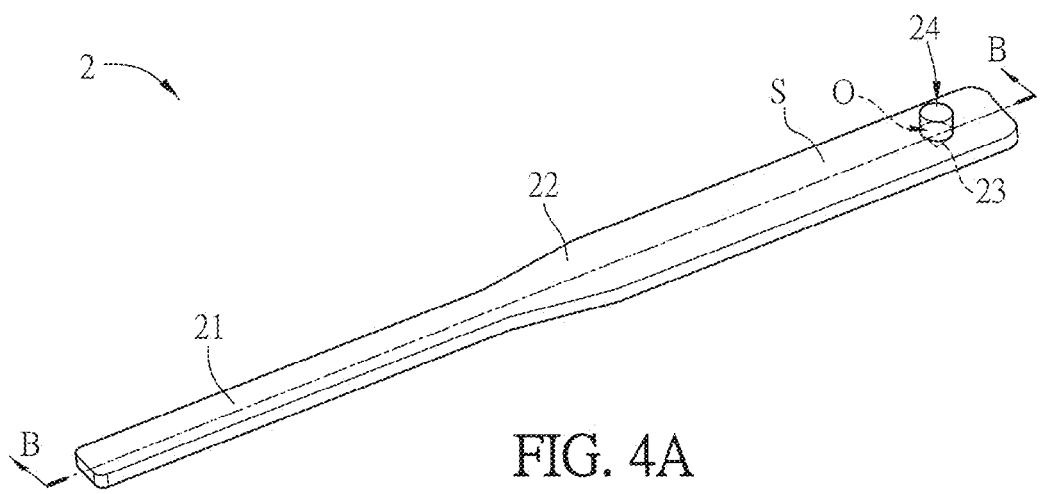
FIG. 4A is a schematic diagram of a detection device according to another preferred embodiment of the invention.
Figure 4B:
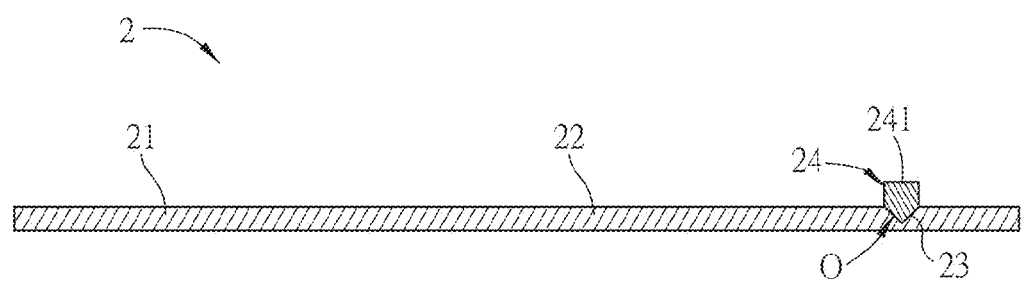
FIG. 4B is a sectional view along the line B-B of FIG. 4A.

The above mentioned aspect of the detection device 1 is not to limit the scope of the invention. FIG. 4A is a schematic diagram of a detection device 2 according to another preferred embodiment of the invention, and FIG. 4B is a sectional view along the line B-B of FIG. 4A. With reference to FIGS. 4A and 4B, the detection device 2 is mostly the same as the previous detection device 1b, but the reaction portion 23 of the detection device 2 includes an accommodating space O and a bulk body 24. The accommodating space O is formed on a surface S of the xylem fiber substrate by physical processing. In this embodiment, at least a part of the bulk body 24 is disposed in the accommodating space O, and it is perpendicular to the long axis direction of the detection device 2. Accordingly, the bulk body 24 can provide an extended flow channel for the test sample. In practice, the enzyme reagent can be disposed at one surface 241 of the bulk body 24, and the test sample is transmitted from the sampling portion 21 to the reaction portion 23 and the bulk body 24 through the transmission portion 22 by capillary action.

To be noted, since the detection device 2 has additional bulk body 24 perpendicular to the reaction portion 23, it can act as a three-dimensional detection device in view of the flowing direction of the test sample.

The xylem fiber substrate of this embodiment is a bamboo material, and the material of the bulk body 24 is a woody material such as birch, aspen or pine materials. Preferably, the densification property of the bulk body (woody material) is greater than that of the reaction portion (bamboo material). The term "densification property" represents the densification of the components (e.g. fiber) in the woody and bamboo materials. When the test sample flows from the reaction portion 23 to the bulk body 24 by capillary action, the flow speed thereof will be slowed down due to the different densification properties. Accordingly, the flow speed can be controlled in the detection, and the test sample can have enough time the finish the desired reaction with the chemical reagent, thereby improving the detection effect of the detection device 2. Of course, the densification properties of the bulk body 24 and the reaction portion 23 are not limited in this invention, and the user can design the desired configurations depending on the actual requirement.

In practice, the material of the bulk body 24 can be the purified α-cellulose. When the proportion of α-cellulose in the bulk body 24 is greater than that in the xylem fiber substrate (preferably the reaction portion 23), the hydrophilic property of the bulk body 24 is better than that of the reaction portion 23. Accordingly, when the test sample flows from the reaction portion 23 to the bulk body 24 by capillary action, the flow speed thereof will increase due to the difference of the hydrophilic properties. In other words, the above design of the bulk body 24 can increase the reaction time of the test sample and speed up the total reaction so as to reduce the detection time. Besides, the needed sample amount can be reduced in this embodiment.

In addition, the shape of the bulk body 24 is, for example but not limited to, cylinder. In practice, the shape of the bulk body 24 can also be a plate shape, and it depends on the structure of the reaction portion 23.

Figure 5A:
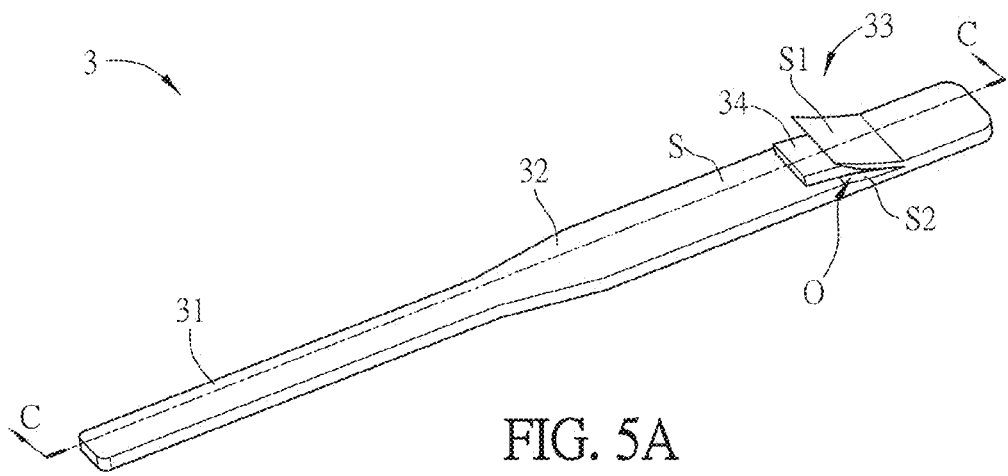
FIG. 5A is a schematic diagram of a detection device according to another preferred embodiment of the invention.
Figure 5B:
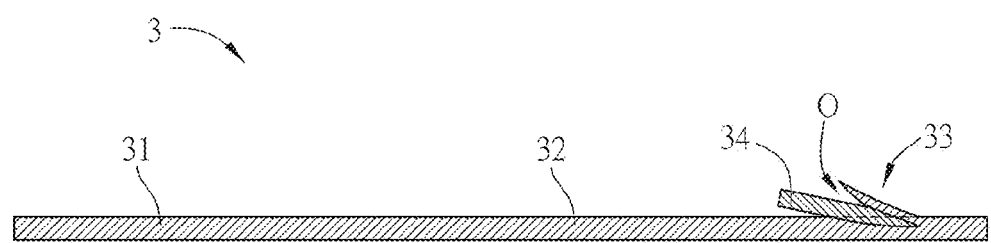
FIG. 5B is a sectional view along the line C-C of FIG. 5A.

In another embodiment, the reaction portion can also be extended by the configurations as shown in FIGS. 5A and 5B, and FIG. 5B is a sectional view along the line C-C of FIG. 5A. In this embodiment, the detection device 3 is mostly the same as the previous detection device 1, but the reaction portion 33 includes an accommodating space O, which is formed by, for example, cutting a part of the detection device 3. Herein, the accommodating space O is disposed between an opened part S1 and a main part S2 of the xylem fiber substrate, and the opened part S1 is at least partially connected to the main part S2. Accordingly, the accommodating space O has a V-shaped structure. When the bulk body 34 is disposed in the accommodating space O, the detection device 3 can also provide an extended flow channel for the test sample, and the test sample is transmitted from the sampling portion 31 to the reaction portion 33 and the bulk body 34 through the transmission portion 32 by capillary action. The materials and implements of the bulk body 34 are mostly the same as those of the above embodiment, so the detailed description thereof will be omitted.

To be noted, the method for disposing the bulk body 24, 34 in the reaction portion 23, 33 is not limited, and any approach capable of contacting the bulk body 24, 34 with the reaction portion 23, 33 is applicable. Besides, the bulk body 24, 34 can be disposed in the reaction portion 23, 33 by embedding, wedging or adhering.

Furthermore, the bulk body 24, 34 can provide an extended flowing area for the test sample, so the operator can easily observe and analyze the detection result on the reaction portion 23, 33. Preferably, when the bulk body 24, 34 is detachable from the reaction portion 23, 33, the bulk body 24, 34 can be taken out of the reaction portion 23, 33 after the reaction for performing any other analysis.

Figure 6A:
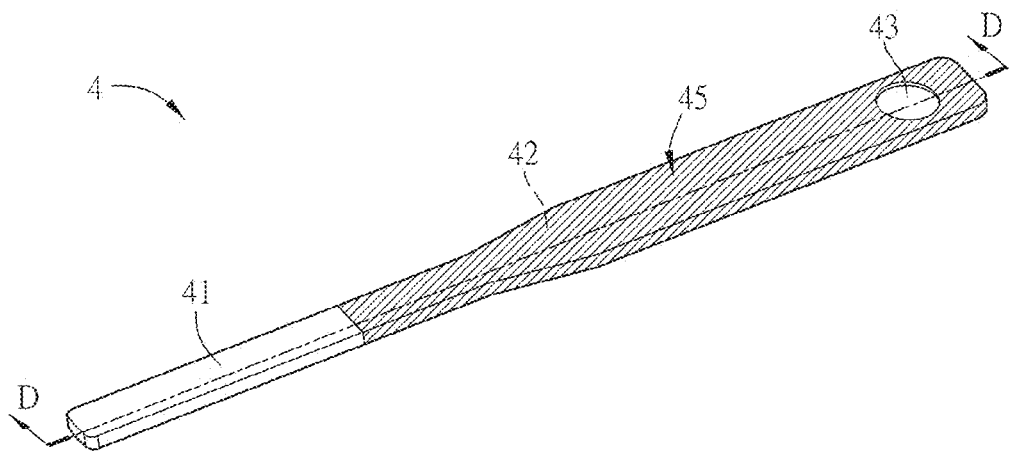
FIG. 6A is a schematic diagram of a detection device according to another preferred embodiment of the invention.
Figure 6B:
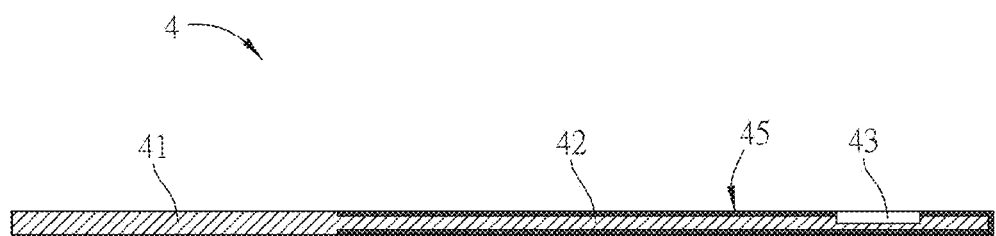
FIG. 6B is a sectional view along the line C-C of FIG. 6A.

FIG. 6A is a schematic diagram of a detection device 4 according to another preferred embodiment of the invention, and FIG. 6B is a sectional view along the line DG-DG of FIG. 6A. With reference to FIGS. 6A and 6B, the detection device 4 is mostly the same as the previous detection device 1, but the transmission portion 42 and the reaction portion 43 of the detection device 4 are processed by additional surface treatment (the dark region 45 of FIGS. 6A and 6B). Herein, the surface treatment is, for example but not limited to, a hydrophobic treatment. The used hydrophobic reagent includes, for example but not limited to, PDMS (polydimethylsiloxane), which is coated on at least part surfaces of the transmission portion 42 and the periphery of the reaction portion 43. In this embodiment, the dark region 45 covers the surfaces of the entire transmission portion 42 and the periphery of the reaction portion 43, while only the reaction portion 43 is exposed for easy observation. The above additional surface treatment can define and minimize the hydrophilic areas contained in the transmission portion 42 and the reaction portion 43, so that when the test sample is transmitted from the sampling portion 41 to the reaction portion 43 and the bulk body 44 through the transmission portion 42 by capillary action, the test sample can be precisely transmitted to the reaction portion 43 via the hydrophilic areas and then properly react with the enzyme reagent.

The hydrophobic treatment is not limited. In practice, it is also possible to coat a photoresist layer on the hydrophilic detection device 4 to achieve the desired treatment. In more specific, when a SU-8 epoxy-based negative photoresist is coated on the detection device 4, the areas irradiated by UV light will not be dissolved in the developing solution so as to form the hydrophobic areas while the areas that is not irradiated by UV light can be exposed and express the original hydrophilic property. To be noted, the above methods and any similar method are well known to the skilled person in the art, so the detailed description thereof will be omitted.

In addition, it is also possible to dip the reaction portion 13 into the enzyme reagent solution for attaching to the enzyme reagent in the reaction portion 13. In more specific, the enzyme reagent can be attached to the reaction portion 13 due to the capillary action of the xylem fiber substrate and the vascular tissue of the plant fiber.

Using the above-mentioned detection device to perform biomedical and food safety detections will be illustrated by the following examples. To be noted, the follow test samples can all be detected by any one of the detection devices 1, 2, 3 and 4 of the above embodiments.

Nitrates are one of the most detected targets in food safety detection. Nitrates are naturally generated substances in nitrogen cycle and generally exist in vegetables and fruits. The concentration of nitrate in the vegetables and fruits depends on the plant species and growing conditions. About 5% of nitrate in the vegetables and fruits will be reduced by saliva or intestinal microorganisms to nitrite, which is easily transformed to the carcinogen "nitrosamines". Besides, the low concentration gastric acid in infant body may transform the excessive nitrates into nitrites. Accordingly, if an infant and young child ingests a large number of foods containing nitrates, the ingested nitrites will be transformed into nitrates and then bound with hemes, thereby decreasing the oxygen carrying function of hemes. This issue will result in hypoxia and thus lead to acquired blue baby syndrome. Therefore, the detection device of the embodiment utilizes the enzyme reagent capable of reacting with nitrate groups to perform the subsequent analysis and interpretation.

Furthermore, when the detection device is applied to detect nitrate groups, the enzyme reagent includes nitrate reductase, sulfanilamide, citric acid, and N-(1-naphthyl) ethylenediamine. If the test sample contains the nitrate groups (nitrates), the color reaction will initiate and then the qualitative test can be performed.

To be noted, the applications for food safety detection are not limited to the above examples, and the detection device of the embodiment can also be applied to other food additives such as bleaches. In more detailed, the food bleaches may include hydrogen peroxide ($H_2O_2$). Although hydrogen peroxide is allowed to be used in food product processes (excluding wheat powder and its related products) for the purpose of sterilization and bleaching, the final food products are not allowed to contain any residual hydrogen peroxide. This is because the boiling point of hydrogen peroxide is too high (152° C.), so the residual hydrogen peroxide cannot be removed by boiling water. If the user eats the food products containing hydrogen peroxide all the time, it may be harmful to the health thereof. Therefore, the detection device 1 of this embodiment can play a critical role for detecting and guarding the above food additives. The specific aspects can be varied according to the source of the detected target such as the food raw materials or soup. The reaction portion can be configured with a proper detection reagent corresponding to these potential test samples for executing the desired detection. Similarly, the location and amount of the detection reagent can be designed depending on the actual requirement, and this invention is not limited.

When the detection device is applied to detect hydrogen peroxide, the used enzyme reagent includes horseradish peroxidase and potassium iodide. If the test sample contains hydrogen peroxide, it will react with the enzyme reagent so that the detection device shows a specific color followed by a proper qualitative test.

Besides, the detection device of the invention can be further applied to biomedical detection. When the detection device is applied to the biomedical detection, the test sample can be, for example but not limited to, the saliva, blood, urine or other body fluids of a patient, and the test target can be, for example but not limited to, glucose, glycogen, or lactic acid. The value of glucose in the patient's blood can be used to interpret the blood glucose level, while the values of glycogen and lactic acid can be used to assess the basic physiological condition of the patient. This simple detection method is benefit for many patients, especially for the patients need special home cares. Accordingly, it is possible to monitor the situation of the patient any time, so that the introduction of the detection device can not only improve the quality of life, but also expand the scope of medical care.

When the detection device is applied to detect glucose, the used enzyme reagent includes glucose oxidase, horseradish peroxidase, 4-aminoantipyrine, 4-(Dimethylamino)benzoic acid and polyethylene glycol (PEG). If the test sample contains glucose, it will react with the enzyme reagent so that the detection device shows a specific color followed by a proper qualitative test.

When the detection device is applied to detect glycogen, the used enzyme reagent includes amyloglucosidase, glucose oxidase, horseradish peroxidase and potassium iodide. If the test sample contains glycogen, it will react with the enzyme reagent so that the detection device shows a specific color followed by a proper qualitative test.

When the detection device is applied to detect lactic acid, the used enzyme reagent includes lactate dehydrogenase, 2-(4-Iodophenyl)-3-(4-nitrophenyl)-5-phenyltetrazolium chloride (INT), NAD and phenazine methosulfate (PMS). If the test sample contains lactic acid, it will react with the enzyme reagent so that the detection device shows a specific color followed by a proper qualitative test.

Figure 7:
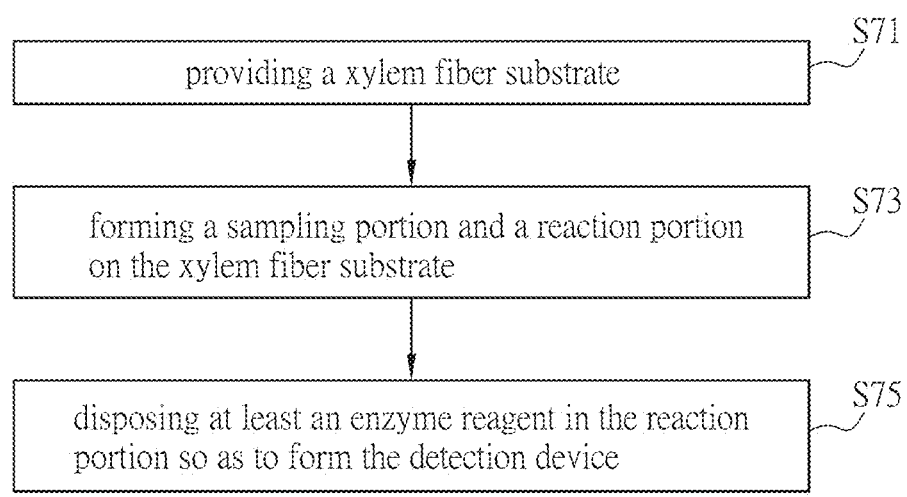
FIG. 7 is a flow chart of a manufacturing method for a detection device according to a preferred embodiment of the invention.

FIG. 7 is a flow chart of a manufacturing method for a detection device according to a preferred embodiment of the invention. Referring to FIG. 7, the manufacturing method for a detection device of the embodiment includes the following steps of: providing a xylem fiber substrate (S71); forming a sampling portion and a reaction portion on the xylem fiber substrate (S73); and disposing at least an enzyme reagent in the reaction portion so as to form the detection device (S75). The step S71 of providing the xylem fiber substrate includes to provide a raw material containing xylem fiber and to physically process the raw material to extract the xylem fiber substrate. Any applicable physically process is acceptable, and this invention is not limited. In addition, the method for forming the sampling portion and the reaction portion is, for example but not limited to, slightly processing the xylem fiber substrate by physical method so as to define the location of each portion. Different manufacturing methods can be provided for various aspects of detection devices. For example, before the step S71, the manufacturing method may further include a step of shaping the xylem fiber substrate to a shape of stirring rod, a toothpick or a chopstick. In more detailed, the xylem fiber substrate can be physically processed to be cut and shaped into a plate shape or a block shape. In practice, when the detection device is a toothpick for example, one end of the detection device is cut into a sharp tip for providing the function of toothpick. To be noted, the above mentioned aspects of detection devices can all be manufactured based on the principle of the disclosed manufacturing method of the embodiment with any proper modification according to the actual structure and requirement. The steps of the manufacturing method for the detection device and the components thereof have been discussed in the above embodiments, so the detailed descriptions thereof will be omitted here.

The actual operation and effect of the detection devices 1, 2 and 3 will be discussed in the following experimental examples. To be noted, the following examples are for illustrations only so that the skilled person can realize and repeat this invention. Of course, the detection devices of other embodiments can also be used to achieve the same goal, and this invention is not limited.

Experimental Example 1

Detecting Glucose by the Detection Device 3

The enzyme reagent is dropped by micropipette onto the reaction portion 33 of the bulk body 34. The enzyme reagent includes 2 µL of 75 U/mL glucose oxidase (X-S type, Sigma Aldrich, St. Louis, Mo.), 15 U/Ml of HRP (VI-A type, Sigma Aldrich, St. Louis, Mo.), 2 mM of 4-aminoantipyrine (99%, Sigma Aldrich, St. Louis, Mo.), 10 mM of 4-(Dimethylamino)benzoic acid (98%, Sigma Aldrich, St. Louis, Mo., and 3% PEG (molecular weight 35,000 g/mol, Sigma Aldrich, St. Louis, Mo.). After adding the enzyme reagent, the detection device 3 is dried for 15 minutes at 25° C. Then, the sampling portion 31 of the detection device 3 is used to contact the test sample. The test samples include glucose solution of different concentrations (0 mM, 2.5 mM, 5 mM, 7.5 mM and 10 mM) in distilled deionized water. Waiting for 5 minutes, the color intensity of the bulk body 34 is determined by ImageJ analysis software.

Figure 8:
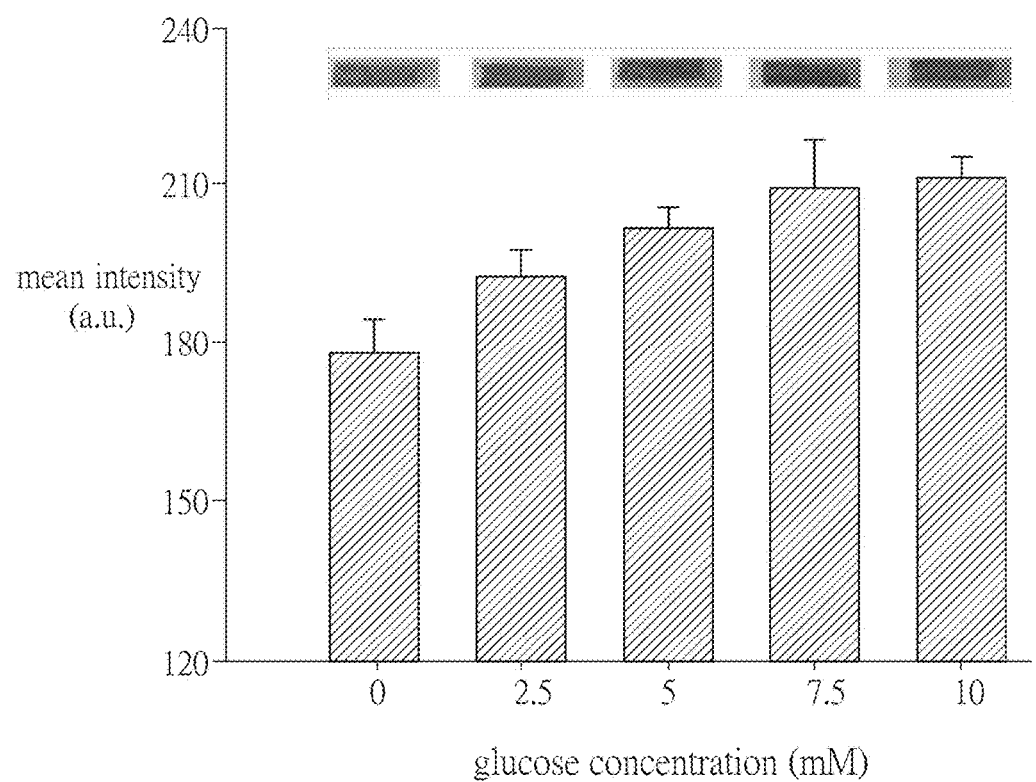
FIG. 8 is a schematic chart showing the detection results as using the detection device of FIG. 5A to detect glucose.

The analysis result is shown in FIG. 8. After the test sample reacts with the enzyme reagent, the test result indicates that the detected mean intensity (which is represented in an Arbitrary Unit, a.u.) of the color reaction increases as the glucose concentration increases. In other words, the detection device 3 can effectively perform the detection of glucose.

Experimental Example 2

Detecting Hydrogen Peroxide by the Detection Device 1

To be noted, the xylem fiber substrate for manufacturing the detection device 1 is optionally made by a bamboo. The enzyme reagent is dropped by micropipette onto the reaction portion 13. The enzyme reagent includes 2 µL of potassium iodide (0.6M) and 1.5 U/mL HRP. After adding the enzyme reagent, the detection device 1 is dried for 2 minutes at 25° C. Then, the sampling portion 11 of the detection device 1 is used to contact the test sample. The test samples include hydrogen peroxide solution of different concentrations (0%, 0.313%, 0.625%, 1.5% and 3%). Waiting for 5 minutes, the color intensity of the reaction portion 13 is determined by ImageJ analysis software.

Figure 9:
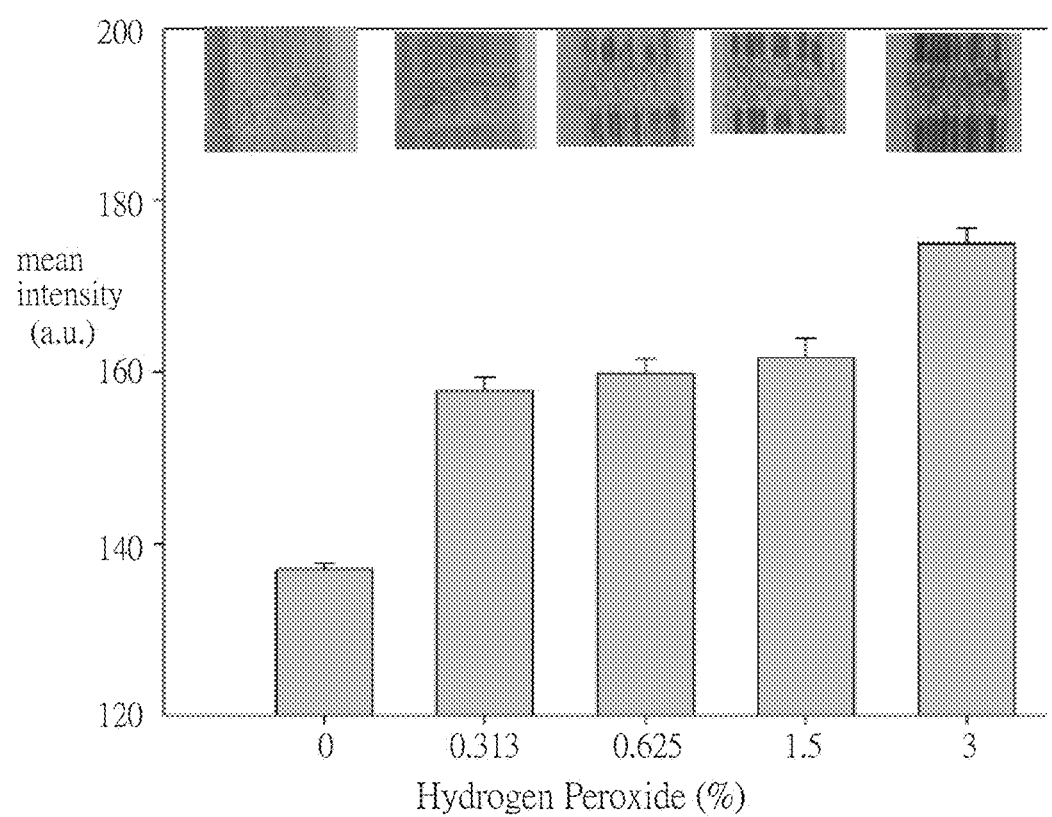
FIG. 9 is a schematic chart showing the detection results as using the detection device of FIG. 1A to detect hydrogen peroxide.

The analysis result is shown in FIG. 9. After the test sample reacts with the enzyme reagent, the test result indicates that the detected mean intensity (which is represented in an Arbitrary Unit, a.u.) of the color reaction increases as the hydrogen peroxide concentration increases.

In other words, the detection device 1 can effectively perform the detection of hydrogen peroxide.

Experimental Example 3

Detecting Lactic Acid by the Detection Device 2

To be noted, the xylem fiber substrate for manufacturing the detection device 2 is optionally made by a bamboo, while the bulk body 24 is optionally made by α-cellulose. The enzyme reagent is dropped by micropipette onto the reaction portion 23 of the bulk body 24. The enzyme reagent includes 6 μL of lactate dehydrogenase (500 U/mL), 1.95 mM of INT(2-(4-Iodophenyl)-3-(4-nitrophenyl)-5-phenyltetrazolium chloride), 3.75 mM of NAD, and 0.81 mM of phenazine methosulfate (PMS). After adding the enzyme reagent, the detection device 2 is dried for 2 minutes at 25° C. Then, the sampling portion 21 of the detection device 2 is used to contact the test sample. The test samples include lactic acid solution of different concentrations (0 mM, 0.5 mM, 5 mM and 50 mM). Waiting for 5 minutes, the color intensity of the bulk body 24 is determined by ImageJ analysis software.

Figure 10:
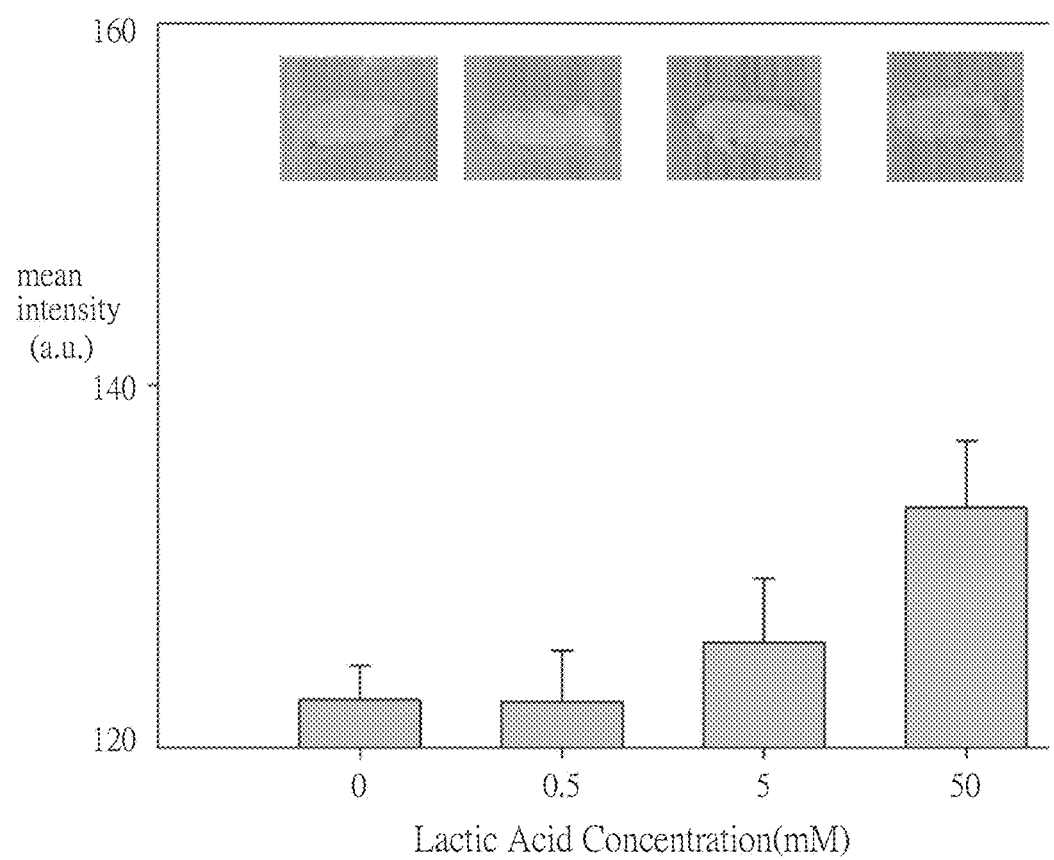
FIG. 10 is a schematic chart showing the detection results as using the detection device of FIG. 4A to detect lactic acid.

The analysis result is shown in FIG. 10. After the test sample reacts with the enzyme reagent, the test result indicates that the detected mean intensity (which is represented in an Arbitrary Unit, a.u.) of the color reaction increases as the lactic acid concentration increases. In other words, the detection device 2 can effectively perform the detection of lactic acid.

In summary, the detection device of the present invention has a reaction portion containing the enzyme reagent for effectively detecting a specific test target such as the concerned nitrate in food safety or the glucose detection in the biomedical detection field. The detection device includes a main structure composed of xylem fiber substrate, which has excellent absorptive property for water molecules, so that the capillary phenomenon of the liquid test sample in the detection device can be enhanced.

In addition, the conventional testing strips, which are made by multiple processes, may contain some residual prohibited or harmful chemical reagents used in the processes, so the food products cannot be served after being detected by the conventional testing strips. In contrary, the detection device of the invention is made of the natural xylem fiber substrate, which has much less influence to the test sample, so the test sample can be still served after the detection. Besides, the present invention also has the advantages of lower cost and easy production. Preferably, the xylem fiber substrate has a strengthened mechanical structure and better pH durability than the conventional testing strips (made by papers).

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A detection device, comprising:
a xylem fiber substrate configured with:
a sampling portion;
a reaction portion having at least an enzyme reagent; and
a transmission portion, wherein the sampling portion, the transmission portion and the reaction portion are adjacently disposed in sequence,
wherein, the sampling portion absorbs a test sample, and the test sample moves on the xylem fiber substrate to the reaction portion and reacts with the enzyme reagent,
wherein the reaction portion has an accommodating space and a bulk body, the accommodating space is formed on a surface of the xylem fiber substrate, at least a part of the bulk body is disposed in the accommodating space, and the enzyme reagent is disposed on the bulk body, and
wherein the accommodating space is disposed between two separate parts on the surface of the xylem fiber substrate, and the two separate parts are at least partially connected to each other.

2. The detection device of claim 1, wherein the xylem fiber substrate comprises cellulose, lignin or hemicellulose.

3. The detection device of claim 1, wherein the enzyme reagent comprises a glucose reagent, a lactic acid reagent, a hydrogen peroxide reagent, a glycogen reagent or a nitrate reagent.

4. The detection device of claim 1, wherein the detection device is a stirring rod, a toothpick or a chopstick.

5. The detection device of claim 1, wherein the proportion of α-cellulose in the bulk body is greater than that in the reaction portion.

6. The detection device of claim 1, wherein the densification property of the bulk body is greater than that of the reaction portion.

7. A manufacturing method for a detection device, comprising steps of:
providing a xylem fiber substrate;
forming a sampling portion and a reaction portion on the xylem fiber substrate;
disposing at least an enzyme reagent in the reaction portion so as to form the detection device;
forming a transmission portion on the xylem fiber substrate, wherein the sampling portion, the transmission portion and the reaction portion are adjacently disposed in sequence,
forming an accommodating space and a bulk body in the reaction portion, wherein the accommodating space is formed on a surface of the xylem fiber substrate, and at least a part of the bulk body is disposed in the accommodating space; and
disposing the enzyme reagent on the bulk body,
wherein the accommodating space is formed between two separate parts on the surface of the xylem fiber substrate, and the two separate parts are at least partially connected to each other.

8. The manufacturing method of claim 7, wherein the step of providing the xylem fiber substrate comprises to provide a raw material containing xylem fiber and to physically process the raw material to extract the xylem fiber substrate.

9. The manufacturing method of claim 7, wherein the xylem fiber substrate comprises cellulose, lignin or hemicellulose.

10. The manufacturing method of claim 7, further comprising, before the step of providing the xylem fiber substrate, a step of:
shaping the xylem fiber substrate to a shape of stirring rod, a toothpick or a chopstick.

11. The manufacturing method of claim 7, wherein the proportion of α-cellulose in the bulk body is greater than that in the reaction portion.

12. The manufacturing method of claim 7, wherein the densification property of the bulk body is greater than that of the reaction portion.

* * * * *